United States Patent
Filser et al.

(10) Patent No.: US 6,905,293 B1
(45) Date of Patent: Jun. 14, 2005

(54) MACHINE TOOL FOR THE PRODUCTION OF BASE STRUCTURES FOR FALSE TEETH

(75) Inventors: Frank Filser, Oberengstringen (CH); Ludwig Gauckler, Schaffhausen (CH); Peter Kocher, Wallisellen (CH); Heinz Luethy, Neuchâtel (CH); Peter Schaerer, Zurich (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 0 days.

(21) Appl. No.: 10/130,588

(22) PCT Filed: Nov. 22, 2000

(86) PCT No.: PCT/CH00/00623

§ 371 (c)(1),
(2), (4) Date: May 16, 2002

(87) PCT Pub. No.: WO01/39691

PCT Pub. Date: Jun. 7, 2001

(30) Foreign Application Priority Data

Dec. 2, 1999 (EP) .................................. 99811105

(51) Int. Cl.[7] .......................................... B23Q 15/00

(52) U.S. Cl. ..................... 409/84; 409/98; 409/103; 409/124

(58) Field of Search ............................. 409/84, 85, 93, 409/94, 96, 98, 99, 100, 104, 105, 106, 108, 409/113, 114, 116; 433/24; 700/163

(56) References Cited

U.S. PATENT DOCUMENTS

| | | | | |
|---|---|---|---|---|
| 3,922,950 A | * | 12/1975 | Walter | 409/103 |
| 4,317,644 A | * | 3/1982 | Hosoi | 409/98 |
| 4,702,652 A | * | 10/1987 | Rokksku et al. | 409/84 |
| 4,746,251 A | * | 5/1988 | Yoshikawa et al. | 409/84 |
| 5,135,393 A | * | 8/1992 | Eidenbenz et al. | 409/124 |

(Continued)

FOREIGN PATENT DOCUMENTS

EP    0 402 720    6/1990

(Continued)

*Primary Examiner*—A. L. Wellington
*Assistant Examiner*—Dana Ross
(74) *Attorney, Agent, or Firm*—Bachman & LaPointe, P.C.

(57) ABSTRACT

The invention relates to an automatic machine tool, for the production of base structures, for false teeth, in particular, for tooth crowns and/or tooth bridges of exact three-dimensional shape. Said base structures may be fixed to prepared natural and/or artificial tooth stumps. The machine tool comprises a machine frame, or a body, a work piece carrier, with a rotation shaft, at least one digitization unit, at least one machining unit and an electronic arithmetic and control unit for all drive lines. A carrier for the workpiece, a blank, and/or for the machining unit(s), serves as displacement unit, with three translational axes in the x-, y- and z-directions. The digitization of the preparation model and the machining of the blank are carried out on the same machine tool, at different times. The machining paths for the blank are calculated from the measured and stored digitized data and a predetermined material-specific scaling factor, before the machining of the blank.

18 Claims, 3 Drawing Sheets

U.S. PATENT DOCUMENTS 5,184,306 A    2/1993  Erdman et al.
5,192,173 A *  3/1993  Andersson et al. ........... 409/84
5,333,974 A *  8/1994  Matsuura ..................... 409/84

FOREIGN PATENT DOCUMENTS

| | | | | |
|---|---|---|---|---|
| EP | 0 904 742 | 3/1999 | | |
| EP | 1088620 A1 * | 4/2001 | .......... | B23Q 15/00 |
| WO | WO 91/18356 | 11/1991 | | |
| WO | WO 96/05782 | 2/1996 | | |
| WO | WO 97/49524 | 12/1997 | | |
| WO | WO 98/36871 | 8/1998 | | |
| WO | WO 9961202 A1 * | 12/1999 | .......... | B23Q 15/00 |

* cited by examiner

US 6,905,293 B1

MACHINE TOOL FOR THE PRODUCTION OF BASE STRUCTURES FOR FALSE TEETH

BACKGROUND OF THE INVENTION

The invention relates to an automatic machine tool for the production of basic structures for dental prostheses, in particular for dental crowns and/or bridges, of precise three-dimensional shape, which basic structures can be attached to prepared natural and/or artificial stumps, where the machine tool has a machine frame or housing, a workpiece carrier with a rotation shaft, at least one digitisation unit, at least one machining unit and an electronic calculating and control unit for all drive elements. The invention also concerns a process for production of positive basic structures for dental prostheses with the automatic machine tool.

A number of devices and processes are known for the production of artificial dental bridges and crowns which are collectively known as dental prostheses. In principle after dental preparation an impression of the dental stump, dental environment and jaw is taken. A system with a mouth camera is also known which derives the machining data from pictures taken in the mouth without producing impressions.

From the impression by way of a gypsum moulding, a master model can be produced. This master model shows in gypsum the situation in the patient's mouth. On this master model, the dental technician by manual skill produces a model of the basic structure of the dental prosthesis in wax and plastic which melts at low temperature or hardens by polymerisation. This model can be embedded in refractory material, baked and then cast out of metal material. The wax model—this term being also used for plastic—can also be transferred to another material by way of mechanical copy machining in scale 1:1, enlarged or reduced. Here we are interested only in the "copy machining" also with enlargement or reduction. A basic structure of ceramic for dental crowns and/or bridges is dense-sintered and shrunk into the definitive shape such that the basic structure can later be set precisely on the dental stump. By the application of a coating of porcelain (hard ceramic) or plastic on the outer surface of the basic structure, the dental crown or bridge can be individualised as required.

WO, A1 96/05782 describes a manually operable device of analog function for production of dental fillings and similar. The device contained two spindles to rotate a model and a blank. The model and blank must rotate in synchrony. Perpendicular to the axis of rotation of the model and blank, on the model is fitted a probe and on the blank a machining tool. As the model and blank rotate, the probe is brought manually into contact with the model surface. At the same time the machining tool machines the blank correspondingly. As the probe is moved over the entire model surface, a scale copy of the model is produced. The main disadvantages of this embodiment are the non-adjustable scaling i.e. the absence of an enlargement or reduction facility, the manual operation, the necessary precise matching of probe and tool, and the problems in production of bodies with cavities (concave surface form). The device described in WO, A1 96/05782 is therefore not suitable for automatic production of dental crowns and dental bridges of any geometry.

U.S. Pat. No. 5,184,306 discloses an automatic high precision production of objects with complex and individual geometry. These complex objects can for example also be dental crowns or dental bridges, over the digital data values of which are laid ideal geometries taken from a library, for example. These ideal geometries are then adapted to the digital data and changed. The paths for the machining tool are then derived from this. No device is shown as such.

EP, A2 0904742 and other publications disclose devices which consist of two separate machines, each of which has an integrated calculator system. The one device is used for digitisation of the surface of a master model, the other for machining the dental crown and/or bridge from a blank. In such devices there are numerous interfaces. The investment costs for such devices are usually high.

The digitisation of the surface of a master model gives approximately the cavital surface of the basic structure. Cementing gaps and occlusal surfaces of the basic structure must be added during calculation e.g. by way of area- or volume-derived complex three-dimensional models. The working method and working means thus do not correspond to the traditional skilful method of work of a dental technician but still require specially trained experts.

JP, A 1058281 describes a computer-controlled machine tool with a common drive for digitisation and machining units which can be exchanged or used in succession. Measuring and machining take place by means of a CAD/CAM system (computer-aided design, computer-aided manufacturing). The workpiece, preferably a blank of dental material or the model, is held by way of a rotation shaft on its facing side in a casing which is movable in the x and y direction. The measurement or machining tool is mounted to be movable in the z direction mounted on an arm of the machine tool. The measurement and machining covers the entire surface of the model or machined blank including the occlusal outer surface and cavital inner surface.

Other devices also work with CAD/CAM systems. Starting from the digitised data they must perform an area derivation or derivation of the digitised surfaces in the CAD system. Further processing of the data e.g. insertion of standardised intermediate elements from a library by way of CAD is then possible. Working with such systems requires special knowledge and skills and due to the use of standardised intermediate elements is restricted with regard to individuality for the patient situation.

The present invention is based on the task of creating an automatic machine tool of the type described initially and a process for the production of positive basic structures which allows reliable production with a small, easy to operate device. The device and process are in particular suitable for a basic structure of a porous ceramic green product—high strength ceramic after sintering—but also for basic structures of plastic or another material which is easy to machine.

SUMMARY OF THE INVENTION

The foregoing task is achieved according to the invention wherein an automatic machine tool for the production of basic structures for dental prostheses of precise three-dimensional shape is provided wherein basic structures can be attached to prepared natural and/or artificial dental stumps, where the machine tool has a machine frame or housing, a workpiece carrier with a rotation shaft, at least one digitisation unit, at least one machining unit and an electronic calculating and control unit for all drive elements. In accordance with the invention, a carrier for the workpiece, a blank and/or for the machining unit(s) is formed as a movable unit with three translation axes in the x, y and z direction and wherein the rotation shaft has on either end clamping means for securing a blank on one end and a dental preparation model on the other end, respectively.

As the concave inner surfaces for dental crowns and/or bridges should be produced without undercutting, it is sufficient for the workpiece carrier preferably to be movable in the x, y and z direction, i.e. the directions of a rectangular spatial co-ordinate system, with the machining unit fixed. It is controlled so that a linear movement of the preferred workpiece carrier takes place simultaneously and rapidly in two or all three directions. In practice the translation axes are formed as linear rails.

In a movable unit for a workpiece carrier, the function of the translation axis in the y direction can be assumed by the rotation shaft of the workpiece carrier as this is designed to be torque-secure extendable or retractable. Optionally the rotation axis can also be movable as a whole in the axial direction.

The said rotation shaft of the workpiece carrier in a first variant has clamping devices on the face at both ends, on one side for a blank to be machined and at the other end for a dental preparation model. The blank consists for example of at least one of the metal oxide powders $Al_2O_3$, $TiO_2$, MgO, $Y_2O_3$ or a zirconium oxide mixed crystal. For further details on the blank and its machining, reference is made to WO, A1 99/47065. The dental preparation model is usually a positive model but it can also be a negative model.

According to another variant the rotation shaft has only at its free facing side a clamping device for a blank and a dental preparation model. The other end of the rotation shaft is anchored in the movable unit.

If the blank and the preparation model can be clamped on the same facing side of the rotation shaft, the machining and digitisation unit of the machine tool must be exchangeable quickly and easily. This can take place for example with a bayonet fitting, preferably however means for movement are provided e.g. a linear rail or a swivel device with a lock in each working position.

According to a further variant the machine tool can comprise several machining units, suitably two machining units are provided lying opposite each other in relation to the rotation shaft, in particular on the top and bottom, front and rear or left and right, depending on whether the rotation shaft is arranged as usual horizontally or exceptionally vertically.

A machining unit of a machine tool comprises one or more, preferably several, machining tools. The machining tools are not the same but differ for coarse and fine machining, which has an effect on the dimensioning of the tools. Usually, two machining tools are arranged according to geometric considerations. Examples of machining tools in the narrower sense are grinding pins or milling cutters for material removal, or radiant machining tools for working by means of laser or electro-erosion.

As the blanks consist in particular of ceramic material which shrinks on sintering, the input of scaling factors is of essential significance. This can be done manually by way of a keypad connected to the calculator and control unit, preferably however by way of a connected read device for optical, electrical, magnetic or mechanical tactile input.

Constructionally, it is particularly advantageous for the digitisation and machining unit to form the same mechanical, pneumatic, hydraulic or electromagnetic system. With reference to the process for the production of positive basic structures for dental prostheses with the automatic machine tool described above, the task according to the invention is solved in that the digitisation of the preparation model and the machining of the blank take place temporally decoupled on the same machine tool, where before machining the blank, the machining paths for the blank are calculated from the determined and stored digitisation data and a specifiable material-specific scaling factor without the use of a CAD system. Special and further embodiments of the process arise from the dependent claims.

The scaling factor can be exactly 1 but in practice it is usually between 1 and 1.5, in particular between 1.2 and 1.3. It can however also be less than 1, in which case the preparation model is accordingly reduced.

Preferably, a positive dental preparation model is digitised. However, a negative model can also be clamped where the digitised data is converted so that a positive machined blank is produced.

The cavital and occlusal digitisation and conversion into machining paths of the machining unit preferably take place without merging in the electronic control unit, so the use of CAD/CAM is therefore—as already stated—neither necessary nor useful. In other words it is not necessary, starting from the digitised data, to perform an area-derivation or derivation of digitised surfaces in the CAD system. Nor is subsequent processing of the data necessary, e.g. the insertion of standardised intermediate elements from a library by way of CAD. Work on such systems would require special knowledge and skills, and due to the use of standardised intermediate elements would be restricted in relation to the individuality for the patient situation. To digitise the entire surface of the preparation model first a basic setting is performed. Then the rotation shaft is turned once through 180°, or three times through 90°, or five times through 60°.

Evidently, the axis can also be turned about other even or uneven angles until the entire surface of the preparation model has been digitised. Depending on programme the rotation shaft can also be turned forward and back in stages.

For production of a machined blank the same applies, the programme for rotating the rotation shaft can be the same or different from that for digitisation.

The electronic control unit can also calculate the machining paths for mirror-image basic structures for dental prostheses, dental crowns and/or bridges and give these to the machining unit.

It has proved particularly advantageous to perform the process with a fixed machining unit and the workpiece carrier as the only unit movable in the x, y and z direction.

BRIEF DESCRIPTION OF THE DRAWINGS

The invention is explained in more detail with reference to the following drawings wherein.

DETAILED DESCRIPTION

Figure 1:
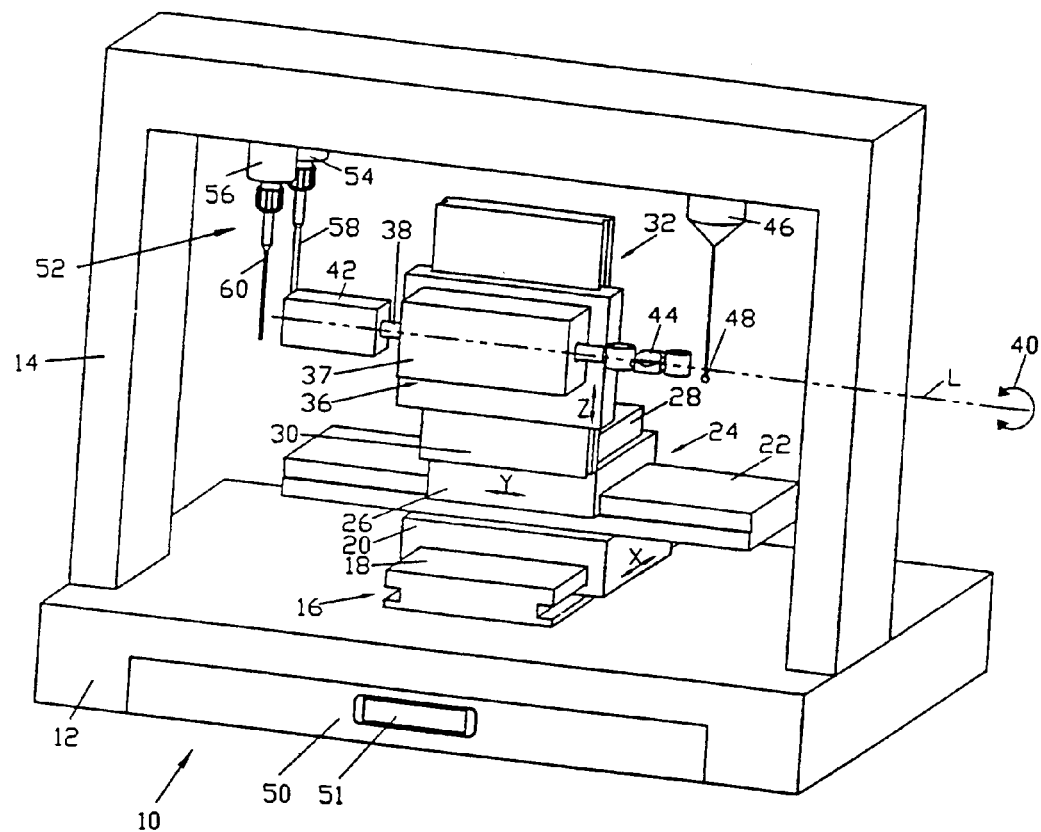
FIG. 1 a machine tool with the main components in perspective view.
Figure 2:
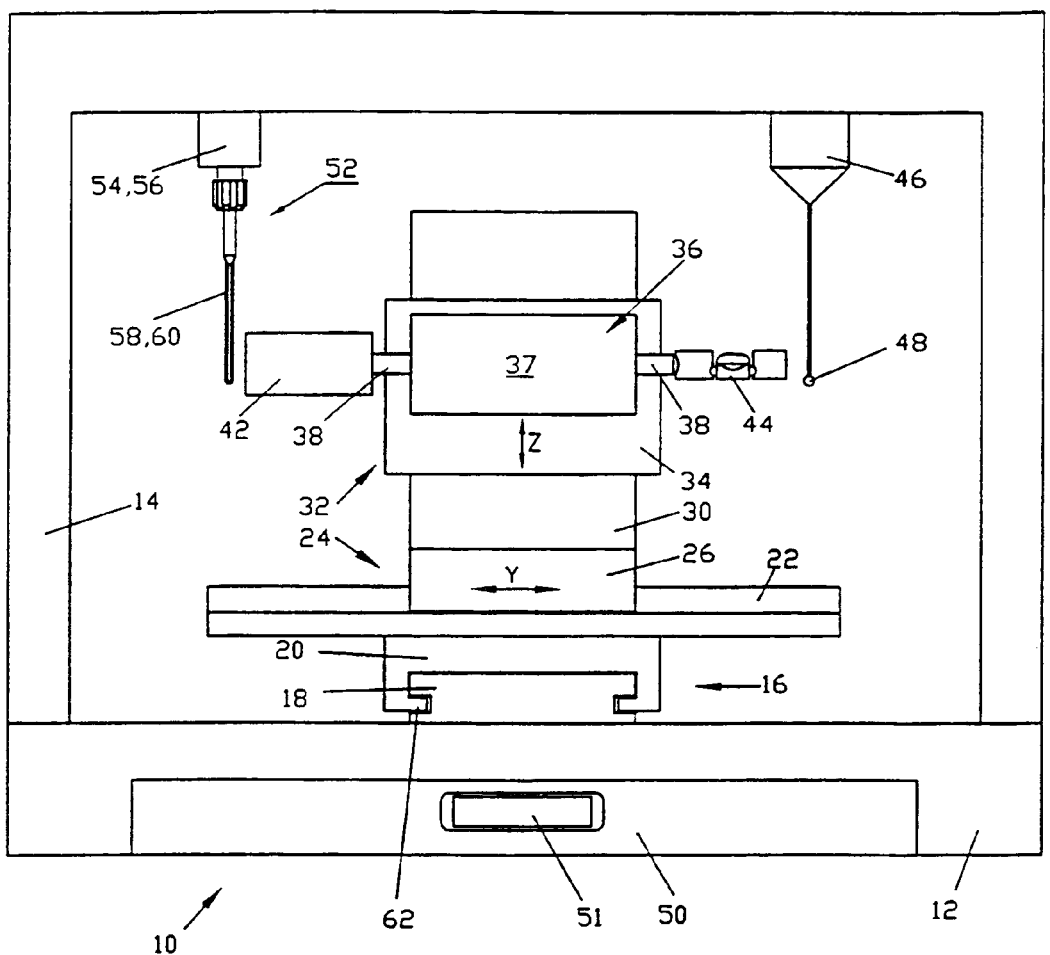
FIG. 2 a front view onto the device according to FIG. 1.
Figure 3:
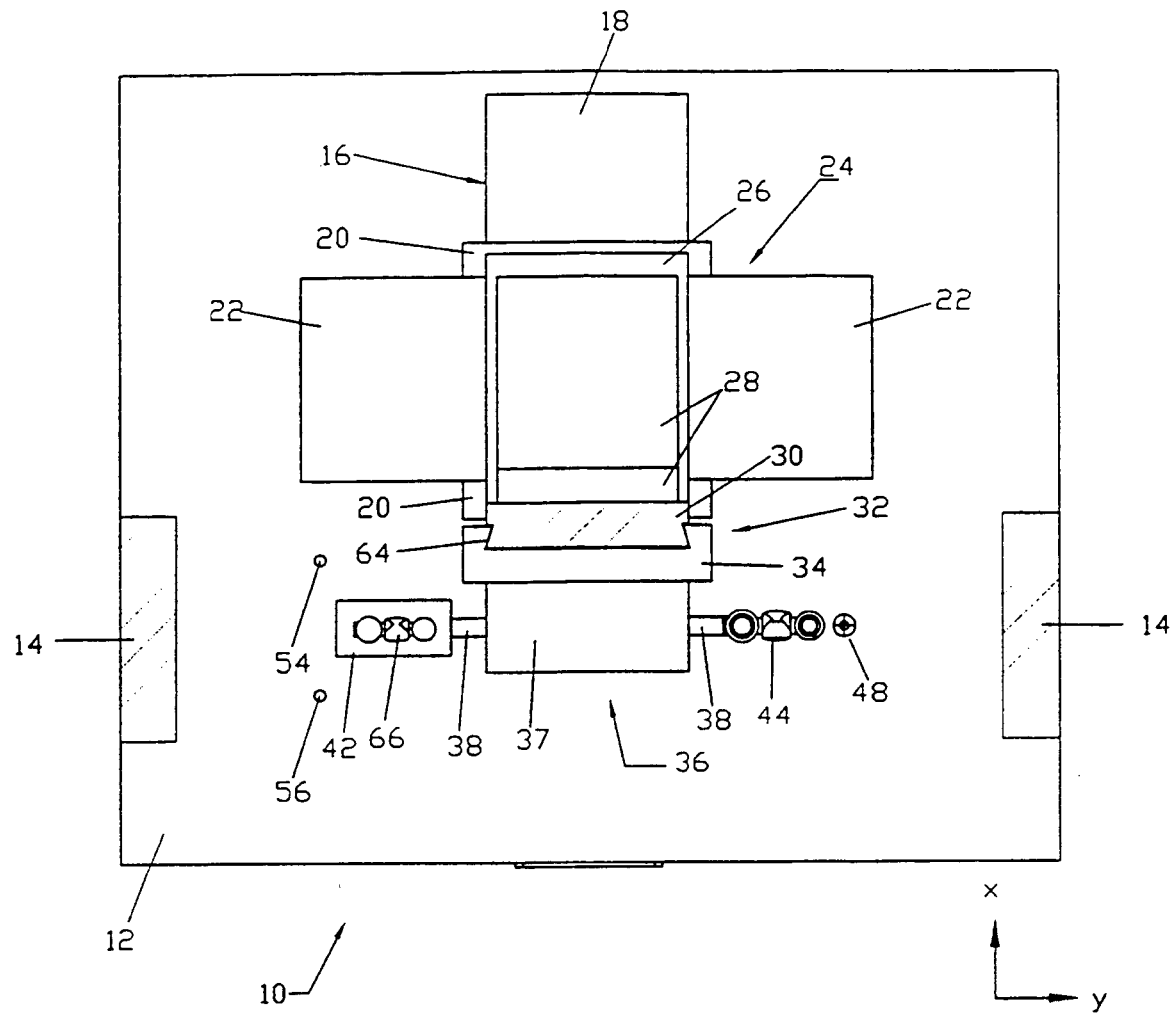
FIG. 3 a top view onto the device according to FIG. 1.

A machine tool 10 according to FIGS. 1 to 3 comprises as the supporting part a machine frame consisting of a base plate 12 and a portal 14.

On the base plate 12 is attached a first linear displacement 16 in the x direction, for example by screwing of a guide rail 18. A double chamfered slide rail 20 can be moved along the guide rail 18 in the x-direction and positioned extremely precisely with means not shown, for example pneumatically, mechanically, hydraulically or electromagnetically.

On the slide rail 26 in the y direction running perpendicular to the x direction is rigidly mounted a guide rail 22 of a second linear displacement 24. Along the guide rail 22 is fitted a slide rail 26 correspondingly chamfered on both sides for precise positioning also with means not shown.

On the slide rail 26 is a fixing bracket 28 for stable holding of a further guide rail 30 of a third linear displacement 32 in the z direction, perpendicular to the x and y directions, with a slide rail 34 also chamfered on both sides and which can also be moved to a precise position with means not shown.

On the slide rail 34 is a rotation unit 36 with in this case a horizontal rotation shaft 38 in a shaft bearing 37. By rotation clockwise or counterclockwise as shown by double arrow 40, this can be rotated to a precise position about a longitudinal axis L. At one end is clamped a cuboid blank 42 of sinterable ceramic material, at the other end the dental preparation model 44.

Obliquely above the dental preparation model 44, a digitisation unit 46 is attached to the portal 14 of the machine frame. This comprises a digitisation probe 48 arranged in the area of the preparation model 44 and made of a cylindrical pin with a ball which works mechanically tactile by scanning the surface of the preparation model 44. Optionally, the digitisation unit 46 can also work by means of a radiation source e.g. a laser.

The data recorded are passed to an electronic calculating and control unit 50, stored there and the machining paths defined for a fixed position machining unit 52. By way of a reader 51 the characteristic data of the blank 42 can be entered in the electronic calculating and control unit 50. In combination with the movable unit, a relative movement of this unit with the blank 42 takes place in relation to the fixed machining unit 52.

The machining unit 52, attached directly or by way of a common carrier to the portal 14, comprises a spindle 54, 56 for each of the coarse machine tool 58 and the fine machine tool 60. Both spindles 54, 56 in the present case have a milling cutter or a grinding pin.

In FIG. 3 the upper arch of the portal 14 has been omitted for clarity reasons.

The stability of the slide rails 20, 26 and 34 is ensured for example by a dovetail form or by two side linear grooves 62 in the side surfaces of the guide rails 18, 22, 30. Corresponding profile parts or cams on the slide rails 20, 26, 34 engage in these linear grooves 62 (FIG. 2).

In FIG. 3 the position of the coarse machining tool 58 and the fine machining tool 60 is indicated, together with the position of the probe 48 or the radiation source. It is also clear that the one half of the vertical guide rail 30 has a dovetail form 64, the two chamfered legs of the slide rail 34 are formed correspondingly.

In the cuboid blank 42, the machined blank 66 is indicated. In contrast to practice common in most cases, this is indicated smaller than the corresponding preparation model 44 i.e. would have a scaling factor less than 1. In practice the machined blank 66 is in most cases designed larger than the corresponding preparation model 44, the scaling factor is greater than 1 i.e. the machined blank 66 shrinks on sintering to the precise dimensions of the preparation model 44.

The three translation axes i.e. the linear guides 16, 24, 32 for the three spatial directions x, y, z are of essential significance for the invention, together with the rotation unit they form a movable unit which serves as a workpiece carrier for the blank 42. Optionally, the machining unit 52 can have the three translatory movable units. Then the workpiece, the blank 42, is not guided to the machining unit 52, but this is guided to the fixed mounted blank 42.

No conventional CAD activities can be performed on the calculating and control unit 50. This is used to control the entire device i.e. to control the movements of the movable unit, collect data on the surfaces from the digitisation unit 46, connect and disconnect the spindles 54 and 56 holding the machining tools 58, 60, and scale the surface data.

Figure 4:
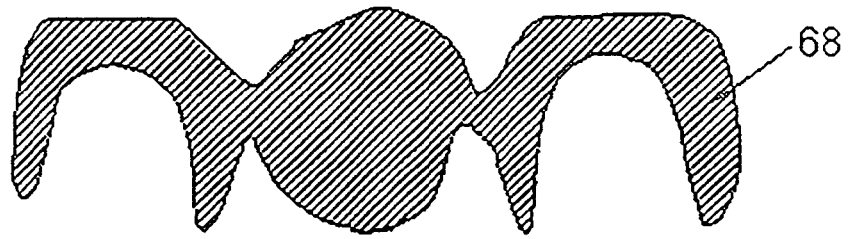
FIG. 4 a section through a basic structure of a dental bridge.

FIG. 4 shows a dense-sintered machined blank 66 in cross section, this is a basic structure 68 for a dental bridge.

The machine tool according to FIGS. 1 to 3 works as follows.

The positive preparation model 44 for the basic structure 68 of a dental bridge is attached on the facing side of the rotation shaft 38. On the opposite facing side is clamped the porous ceramic blank 42. Using the digitisation unit 46 the complete surface of the positive preparation model 44 is transferred digitally to the electronic calculating and control unit 50. Then first the occlusal surface is digitised. Then the preparation model 44 by means of a rotation shaft 38 is turned through a particular angle, in the present case through 1800. Then in the same way the cavital surface of the preparation model 44 is determined. Merging of the occlusal and cavital surfaces of the preparation model 44 in the calculating and control unit 50 is not necessary as the relative position of the occlusal and cavital surfaces is established by the rotation shaft 38.

By entering a scaling factor of 1.2512, the surfaces enlarged for the digital data of the occlusal and cavital surfaces are derived and the tool paths calculated taking into account the geometric data of the coarse machining tool 58 and the fine machining tool 60. The result are machining programmes suitably in the following order:

coarse machining for the occlusal surface (1),
coarse machining for the cavital surface (2),
fine machining for the occlusal surface (3) and
fine machining for the cavital surface (4).

The sequence can also differ e.g. (2), (1), (4), (3) or (1), (3), (2), (4).

The geometric arrangement of the machining tools 58, 60 gives the necessary displacements in the x, y and z direction or a reflection of the data for machining.

The blank 42 is then machined. Taking into account the displacements/reflections, first the coarse machining for the occlusal surface is performed according to the corresponding machining programme with coarse machining tool 58. Then the rotation shaft 38 is rotated through 1800 and taking into account the displacements/reflections, the coarse machining is performed for the cavital surface according to the corresponding machining programme with coarse machining tool 58. Then taking into account the displacements/reflections, fine machining of the cavital surface takes place according to the corresponding machining programme with the fine machining tool 60. Then the rotation shaft 38 is rotated through 1800. Then taking into account the necessary displacements/reflections, the fine machining is performed for the occlusal surface according to the corresponding machining process with fine machining tool 60. The result is a machined blank 66 which corresponds to the positive model enlarged by the scaling factor 1.2512.

Using suitable machine tools it can firstly be advantageous to perform only one machining step per surface (occlusal and cavital), secondly instead two or three or more machining steps per surface can be performed.

The machined blank is removed from the rotation shaft 38. The subsequent working steps are the burning (sintering) of the machined, still porous ceramic blank to its full density and individualisation by burning on hard ceramic (see for example WO, A 99/47065).

As stated by special linear imaging of the data, mirror-image and/or even distorted copies of the preparation model can also be produced from the blank.

What is claimed is:

1. Automatic machine tool for production of basic structures for dental prostheses of precise three-dimensional shape, which basic structures can be attached to prepared natural and/or artificial dental stumps, where the machine tool has a frame means, a workpiece carrier with one common rotation shaft having an axis L for a blank, at least one digitisation unit, at least one machining unit and an electronic calculating and control unit for all drive elements, wherein at least one of the workpiece carrier for the blank and a dental preparation model on the one hand and the machining unit and the digitisation unit on the other hand are on a common movable unit with three linear translation axes in the x, y and z direction, and wherein the one common rotation shaft has on either end clamping means for securing the blank on one end and the dental preparation model on the other end, respectively, wherein the blank and the dental preparation model project from the ends along the axis L and lie on and rotate about the axis L.

2. The machine tool according to claim 1, wherein the workpiece carrier is on a movable unit with three translation axes in the x, y and z direction and the machining unit and the digitisation unit are fixed on the frame means.

3. The machine tool according to claim 1, wherein the workpiece carrier is fixed on the frame means and the machining unit and the digitisation unit are on the common moveable unit with three translation axes in x, y and z direction.

4. The machine tool according to claim 2, including means for varying the length of the rotation shaft in the axial direction (L) in relation to a shaft bearing and forms a translation axis in the y direction.

5. The machine tool according to any of claims 1–3, including a plurality of at least one of the digitisation units and the machining units, lying diagonally opposite each other in relation to the rotation shaft.

6. The machine tool according to any of claims 1–3, wherein the machining unit has a plurality of machining tools, for coarse and fine machining.

7. The machine tool according to any of claims 1–3, wherein the machining unit is equipped with at least one of material removal and radiant machining tools.

8. The machine tool according to any of claims 1–3, wherein the electronic calculating and control unit has at least one of optical, electrical, magnetic and mechanical tactile read device for entering scaling factors.

9. The machine tool according to any of claims 1–3, including at least one of mechanical, pneumatic, hydraulic and electromagnetic drive means for the movable unit, the digitisation unit and the machining unit.

10. Process for production of positive basic structures for dental prostheses with the automatic machine tool according to any one of claims 1–3, wherein the digitisation of the preparation model and the machining of the blank take place temporally decoupled on one machine tool with blank and dental preparation model clamped simultaneously, wherein before machining of the blank, from the determined and stored digitisation data and a preset material-specific scaling factor, the machining paths for the blank are calculated without the use of a CAD system to construct the preparation model.

11. Process according to claim 10, wherein the characteristic blank data is entered in the electronic calculating and control unit, and the dental preparation model of the basic structure and, with the appropriate design of rotation shaft, the blank is clamped, at least the cavital inner surfaces of the preparation model are fully digitised, the digitally recorded surface data converted into machining paths for the machining unit, the blank machined in consecutive steps until the stored end form is achieved, and the machined blank and the preparation model taken from the machine tool.

12. Process according to claim 10, wherein a positive preparation model is digitised.

13. Process according to claim 12, wherein an occlusal and cavital digitisation of the preparation model and conversion into machining paths take place without merging of the occlusal and cavital surfaces in the electronic calculating and control unit.

14. Process according to claim 12, wherein, for digitising the entire surface of the preparation model and production of the machined blank, the rotation shaft is turned from a base position through one of 180°, 90° and 60°.

15. Process according to claim 10, wherein the electronic calculating and control unit calculates the machining paths for a mirror-image basic structure for a dental prosthesis and passes these to the machining unit.

16. Process according to claim 10, wherein a first coarse machining of the occlusal and then the cavital surface of the machined blank take place followed by fine machining of the occlusal and then the cavital surface, wherein the coarse and fine machining are diagonally opposite each other in relation to the rotation shaft.

17. Machine tool according to claim 1, wherein the frame means is at least one of a machine frame and a housing.

18. Machine tool according to claim 1, wherein the dental prostheses is at least one of a crown and a bridge.

* * * * *